(12) United States Patent
Sims et al.

(10) Patent No.: US 11,298,181 B2
(45) Date of Patent: Apr. 12, 2022

(54) ELECTROSURGICAL FORCEPS

(71) Applicant: COVIDIEN LP, Mansfield, MA (US)

(72) Inventors: Grant T. Sims, Boulder, CO (US);
Daniel W. Mercier, Erie, CO (US);
Craig V. Krastins, Arvada, CO (US);
Jennifer L. Rich, Parker, CO (US);
Kelley D. Goodman, Erie, CO (US)

(73) Assignee: Covidien LP, Mansfield, MA (US)

( * ) Notice: Subject to any disclaimer, the term of this patent is extended or adjusted under 35 U.S.C. 154(b) by 341 days.

(21) Appl. No.: 16/454,844

(22) Filed: Jun. 27, 2019

(65) Prior Publication Data
US 2020/0405376 A1  Dec. 31, 2020

(51) Int. Cl.
| *A61B 18/12* | (2006.01) |
| --- | --- |
| *A61B 18/14* | (2006.01) |
| *A61B 18/08* | (2006.01) |
| A61B 18/00 | (2006.01) |

(52) U.S. Cl.
CPC ........ *A61B 18/1445* (2013.01); *A61B 18/085* (2013.01); *A61B 18/1206* (2013.01); *A61B 2018/0063* (2013.01); *A61B 2018/00589* (2013.01); *A61B 2018/00595* (2013.01); *A61B 2018/146* (2013.01); *A61B 2018/1455* (2013.01)

(58) Field of Classification Search
CPC combination set(s) only.
See application file for complete search history.

(56) References Cited

U.S. PATENT DOCUMENTS

| 5,745,997 A | 5/1998 | Berg et al. | |
| --- | --- | --- | --- |
| 8,828,023 B2 | 9/2014 | Neff et al. | |
| 9,005,200 B2 | 4/2015 | Roy et al. | |
| 2008/0215048 A1* | 9/2008 | Hafner | A61B 17/2841 |
| | | | 606/42 |
| 2014/0336635 A1* | 11/2014 | Hart | A61B 17/2804 |
| | | | 606/41 |
| 2016/0058498 A1* | 3/2016 | Goodman | A61B 18/1442 |
| | | | 606/42 |
| 2016/0175033 A1 | 6/2016 | Le | |
| 2017/0196648 A1 | 7/2017 | Ward et al. | |
| 2018/0325580 A1 | 11/2018 | Sims et al. | |

FOREIGN PATENT DOCUMENTS

WO    2016025132 A1    2/2016

* cited by examiner

*Primary Examiner* — Daniel W Fowler

(57) ABSTRACT

An electrosurgical forceps includes first and second shaft members pivotably coupled to one another such that pivoting of the first and second shaft members between spaced-apart and approximated positions pivots jaw members thereof between open and closed positions. A handle of the first shaft member may be moved against a resilient bias of a spring element.

4 Claims, 3 Drawing Sheets

ELECTROSURGICAL FORCEPS

BACKGROUND

The present disclosure relates to electrosurgical instruments and, more particularly, to electrosurgical forceps for grasping, treating, and/or dividing tissue.

TECHNICAL FIELD

A surgical forceps is a plier-like instrument which relies on mechanical action between its jaws to grasp tissue. Electrosurgical forceps utilize both mechanical clamping action and electrical energy to treat tissue, e.g., coagulate, cauterize, and/or seal tissue. Typically, once tissue is treated, the surgeon has to accurately sever the treated tissue. Accordingly, many electrosurgical forceps incorporate a knife configured to effectively sever tissue after the tissue is treated.

The surgical forceps generally includes a pair of shaft members having jaws attached to distal ends thereof. A compressible button may be provided at a proximal end of the one of the shaft members. During clamping of tissue between the jaws, one or both of the shaft members flex toward one another, whereby the proximal end of one shaft member actuates an electrosurgical switch at the proximal end of the other of the shaft members.

SUMMARY

As used herein, the term "distal" refers to the portion that is being described which is further from a surgeon, while the term "proximal" refers to the portion that is being described which is closer to a surgeon. Further, to the extent consistent, any of the aspects described herein may be used in conjunction with any or all of the other aspects described herein.

As used herein, the terms parallel and perpendicular are understood to include relative configurations that are substantially parallel and substantially perpendicular up to about +/−10 degrees from true parallel and true perpendicular.

An electrosurgical forceps provided in accordance with aspects of the present disclosure includes a first shaft member, a second shaft member, and an elongated spring element. The first shaft member has a first jaw member secured to and extending distally from the first shaft member. The first shaft member has a proximal end portion supporting a handle. The second shaft member is pivotably coupled to the first shaft member and has a second jaw member secured to and extending distally from the second shaft member. The second shaft member has a proximal end portion supporting an activation switch. The elongated spring element is supported in the proximal end portion of the first shaft member. The handle is configured to flex the elongated spring element and urge the proximal end portion of the first shaft member into engagement with the activation switch.

In aspects, the elongated spring element may have a proximal end and a distal end. The proximal and/or distal end of the elongated spring element may be fixed to the first shaft member.

In aspects, the electrosurgical forceps may further include a first capture member and a second capture member. The first capture member may be operably engaged to an inner wall of the proximal end portion of the first shaft member. The proximal end of the elongated spring element may be supported by the capture member. The second capture member may be operably engaged to the inner wall. The distal end of the elongated spring element may be supported by the second capture member.

In aspects, the second shaft member may be rigid along its length.

In aspects, the first and second shaft members may be configured to resist flexing during approximation of the proximal end portions thereof.

In aspects, the elongated spring element may be a cantilever spring.

BRIEF DESCRIPTION OF THE DRAWINGS

Various aspects and features of the present disclosure are described hereinbelow with reference to the drawings wherein like numerals designate identical or corresponding elements in each of the several views.

DETAILED DESCRIPTION

Figure 1:
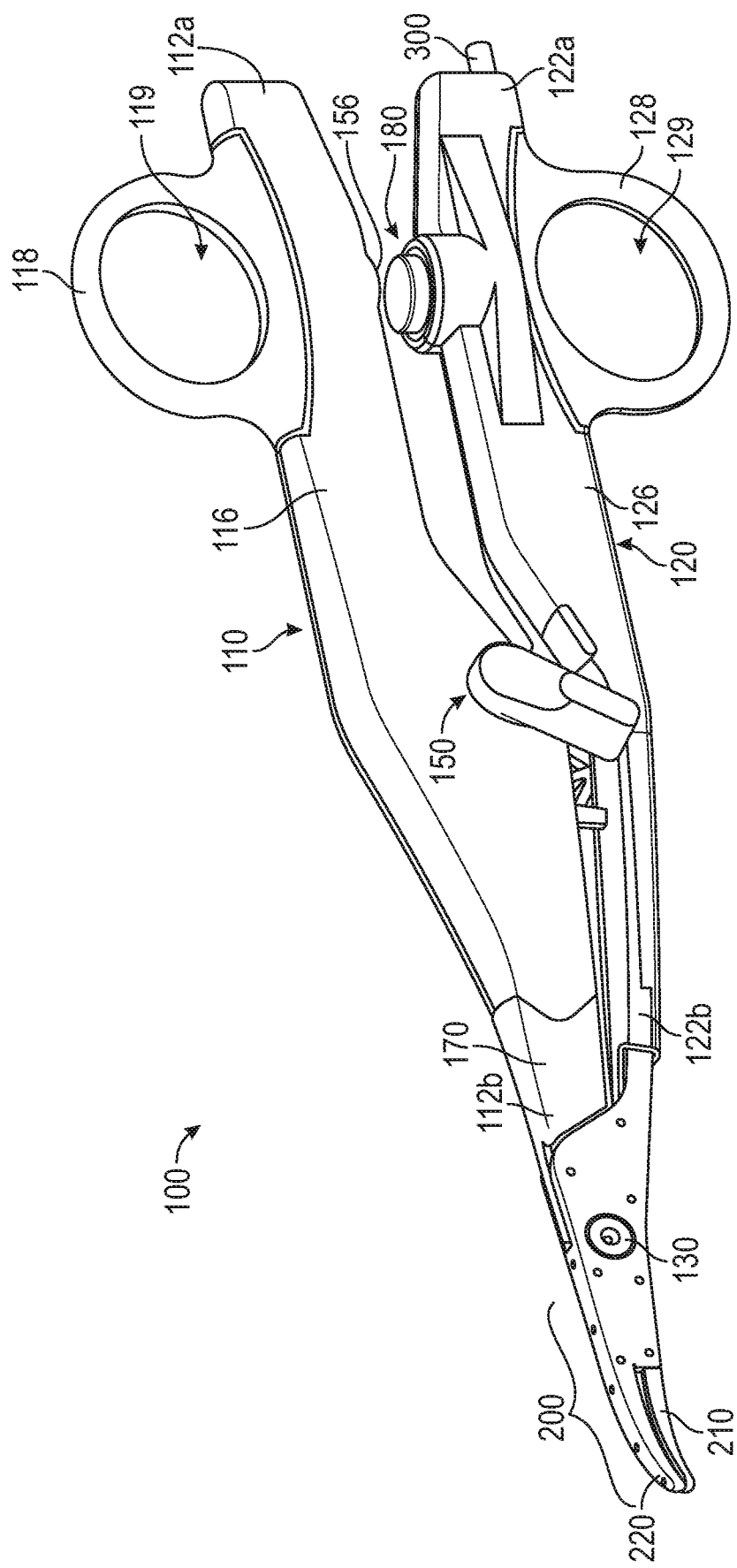
FIG. 1 is a side, perspective view of an electrosurgical forceps provided in accordance with aspects of the present disclosure.
Figure 2:
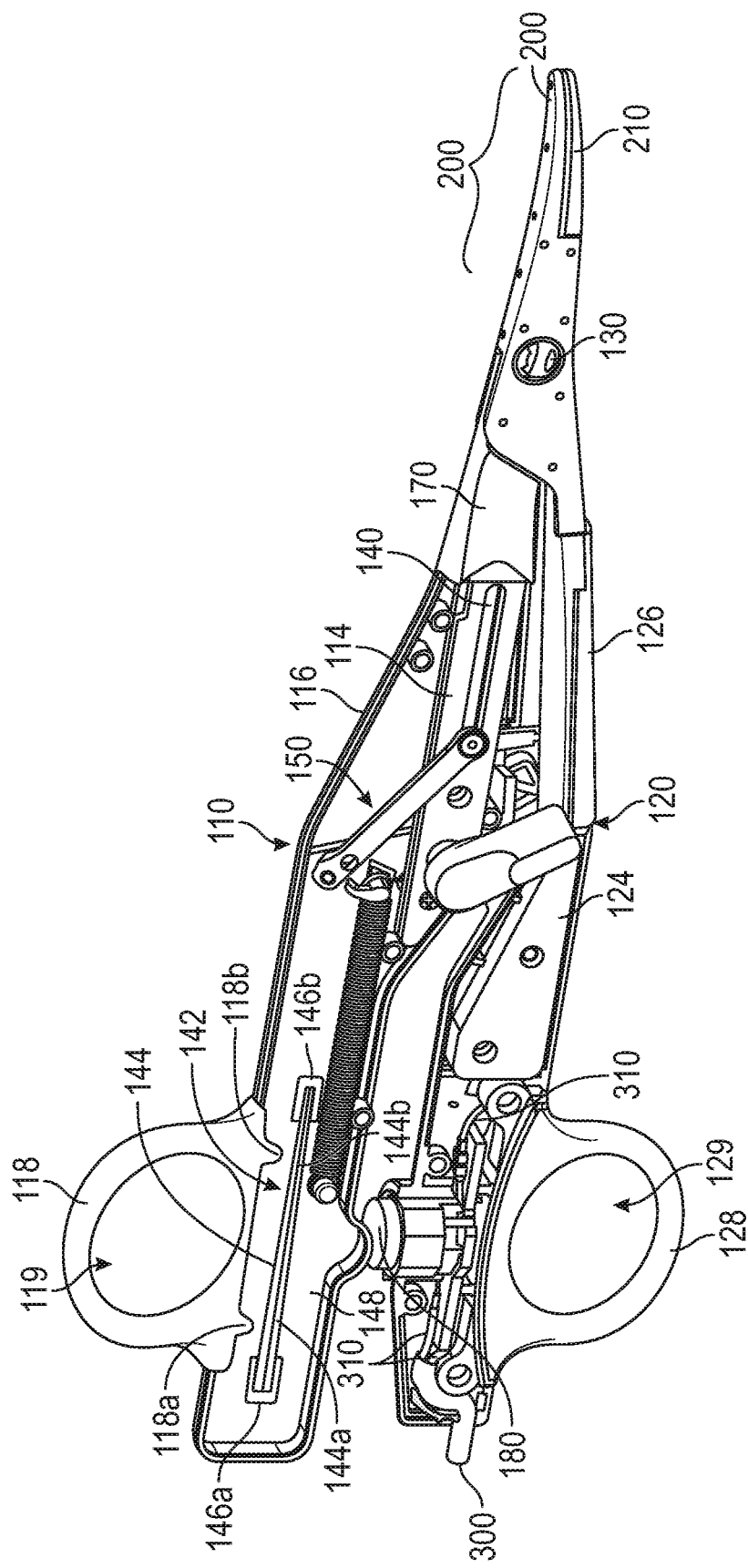
FIG. 2 is a perspective view from one side of the forceps of FIG. 1 with portions of outer housings of first and second shaft members removed to illustrate the internal components therein.

Referring to FIGS. 1 and 2, a forceps 100 provided in accordance with the present disclosure generally includes first and second shaft members 110, 120 and an end effector assembly 200. Shaft members 110, 120 each have a proximal end portion 112a, 122a and a distal end portion 112b, 122b. End effector assembly 200 includes first and second jaw members 210, 220 extending from distal end portions 112b, 122b of shaft members 110, 120, respectively. Forceps 100 further includes a pivot member 130 pivotably coupling first and second shaft members 110, 120 with one another, a knife 140, a knife deployment mechanism 150 for selectively deploying the knife 140 relative to end effector assembly 200, a knife lockout 170 for inhibiting deployment of knife 140 prior to sufficient closure of jaw members 210, 220, and a switch assembly 180 for enabling the selective supply of electrosurgical energy to end effector assembly 100. An electrosurgical cable 300 electrically couples forceps 100 to a source of energy (not shown), e.g., an electrosurgical generator, to enable the supply of electrosurgical energy to jaw members 210, 220 of end effector assembly 200 upon activation of switch assembly 180.

Continuing with reference to FIGS. 1 and 2, each shaft member 110, 120 includes an inner frame 114, 124, an outer housing 116, 126 surrounding at least a portion of the respective inner frame 114, 124, and a handle 118, 128 engaged with the respective outer housing 116, 126 towards proximal end portions 112a, 122a of shaft members 110, 120, respectively. Outer housings 116, 126 enclose and/or operably support the internal components disposed within shaft members 110, 120. More specifically, outer housing 116 of shaft member 110 encloses and supports at least a portion of inner frame 114, knife deployment mechanism 150, and lockout 170, while outer housing 126 of shaft member 120 receives electrosurgical cable 300 and encloses and supports at least a portion of inner frame 124, switch assembly 180, and the lead wires 310 of electrosurgical cable 300. The handles 118, 128 are engaged with outer housings 116, 126 towards proximal end portions 112a, 112b of shaft members 110, 120 and extend outwardly from shaft members 110, 120. Handles 118, 128 define finger holes 119, 129 configured to facilitate grasping and manipulating shaft members 110, 120.

Figure 3:
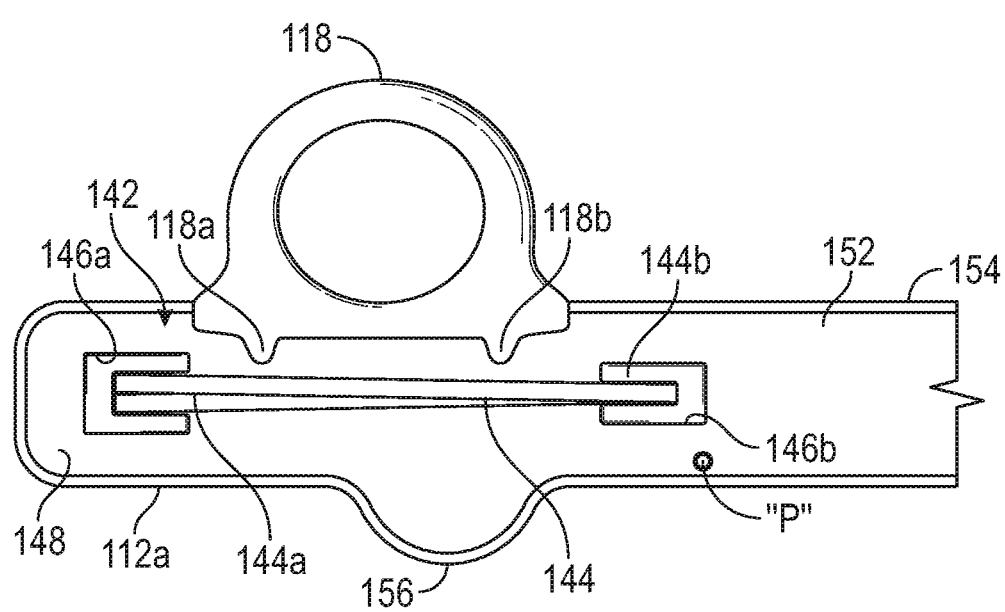
FIG. 3 is a schematic illustration of an embodiment of a spring assembly of the first shaft member shown in FIG. 2.

With reference to FIGS. 2 and 3, the proximal end portion 112a has a protuberance 156 extending outwardly therefrom configured to engage the switch assembly 180. The handle 118 includes a pair of feet 118a, 118b received in the outer housing 116. The feet 118a are supported in the outer housing 116, such that the handle 118 is restricted from proximal or distal movement relative to the outer housing 116 while being translatable along an axis transverse to a longitudinal axis defined by the proximal end portion 112a. In aspects, vertical guide rails (not shown) may be provided that guide the up-down movement of the handle 118 within the outer housing 116. In some aspects, instead of being axially movable, the handle 118 may have a first end (e.g., a distal end) pivotably coupled to the outer housing 116 and a second end (e.g., a proximal end) that selectively engages a spring element 144 as the handle 118 pivots.

The first shaft member 110 has a spring assembly 142 supported in the outer housing 116 beneath the handle 118. In particular, the spring assembly 142 includes an elongated spring element 144, such as, for example, a cantilever spring arm, and a pair of capture members 146a, 146b. In aspects, the spring element 144 may be fixed at only one end. The elongated spring element 144 has opposing proximal and distal ends 144a, 144b fixed in the respective capture members 146a, 146b. The first capture member 146a may be formed with or otherwise fixed to an inner wall 148 of the proximal end portion 112a of the outer housing 116, and the second capture member 146b may be formed with or otherwise fixed to the inner wall 148. Each of the capture members 146a, 146b defines a horizontal slot having received therein the proximal and distal ends 144a, 144b of the elongated spring element 144. In aspects, the proximal and distal ends 144a, 144b of the elongated spring element 144 may be fixed to the proximal end portion 112a via any suitable fastening mechanism, such as, for example, adhesives, bayonet-type, or the like.

In operation, with tissue disposed between the jaws 210, 220, the proximal end portions 112a, 122a of the first and second shaft members 110, 120 are approximated, thereby approximating the jaw members 210, 220 to compress the tissue therebetween. With the tissue compressed between the jaw members 210, 220, the protuberance 156 of the first shaft member 110 may remain spaced from the switch assembly 180, and therefore yet to have activated the switch assembly 180. In this instance, a further approximation of the proximal end portions 112a, 122a is needed to deliver electrosurgical energy to the tissue.

A further application of an approximating force on the handles 118, 128 overcomes the resilient bias of the elongated spring element 144, thereby allowing the handle 118 to translate within the outer housing 116 and cause the proximal end 144a of the elongated spring element 144 to flex relative to the distal end 144b of the elongated spring element 144, thereby providing sufficient closure force on the tissue.

In some aspects, the protuberance 156 may extend from a central region of the elongated spring element 144. In this embodiment, upon exerting a downwardly-oriented threshold force on the elongated spring element 144, via the handle 118, the protuberance 156 is urged closer to and ultimately into engagement with the switch assembly 180. In other aspects, the handle 118 may be flexible. In further aspects, the proximal end portion 112a, 122a of one or both of the first and second shaft members 110, 120 may be coupled to the remaining portions of the first and second shaft members 110, 120 via any suitable biasing member, such as, for example, torsion springs, coil springs, leaf springs, or the like.

For a detailed description of various components and manners of operating forceps 100 of the present disclosure, reference may be made to U.S. Patent Application Publication No. 2018/0325580, filed on May 12, 2017, the entire contents of which is incorporated by reference herein.

The various embodiments disclosed herein may also be configured to work with robotic surgical systems and what is commonly referred to as "Telesurgery." Such systems employ various robotic elements to assist the clinician and allow remote operation (or partial remote operation) of surgical instrumentation. Various robotic arms, gears, cams, pulleys, electric and mechanical motors, etc. may be employed for this purpose and may be designed with a robotic surgical system to assist the clinician during the course of an operation or treatment. Such robotic systems may include remotely steerable systems, automatically flexible surgical systems, remotely flexible surgical systems, remotely articulating surgical systems, wireless surgical systems, modular or selectively configurable remotely operated surgical systems, etc.

The robotic surgical systems may be employed with one or more consoles that are next to the operating theater or located in a remote location. In this instance, one team of clinicians may prep the patient for surgery and configure the robotic surgical system with one or more of the instruments disclosed herein while another clinician (or group of clinicians) remotely controls the instruments via the robotic surgical system. As can be appreciated, a highly skilled clinician may perform multiple operations in multiple locations without leaving his/her remote console which can be both economically advantageous and a benefit to the patient or a series of patients.

For a detailed description of exemplary medical work stations and/or components thereof, reference may be made to U.S. Patent Application Publication No. 2012/0116416 (now U.S. Pat. No. 8,828,023), and PCT Application Publication No. WO2016/025132, the entire contents of each of which are incorporated by reference herein.

Persons skilled in the art will understand that the structures and methods specifically described herein and shown in the accompanying figures are non-limiting exemplary embodiments, and that the description, disclosure, and figures should be construed merely as exemplary of particular embodiments. It is to be understood, therefore, that the present disclosure is not limited to the precise embodiments described, and that various other changes and modifications may be effected by one skilled in the art without departing from the scope or spirit of the disclosure. Additionally, the elements and features shown or described in connection with certain embodiments may be combined with the elements and features of certain other embodiments without departing from the scope of the present disclosure, and that such modifications and variations are also included within the scope of the present disclosure. Accordingly, the subject matter of the present disclosure is not limited by what has been particularly shown and described.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. An electrosurgical forceps, comprising:
   a first shaft member having a first jaw member secured to and extending distally from the first shaft member, the first shaft member having a proximal end portion supporting a handle;
   a second shaft member pivotably coupled to the first shaft member and having a second jaw member secured to and extending distally from the second shaft member, the second shaft member having a proximal end portion supporting an activation switch; and
   an elongated spring element supported in the proximal end portion of the first shaft member, wherein the handle is configured to flex the elongated spring element and urge the proximal end portion of the first shaft member into engagement with the activation switch, wherein the elongated spring element has a proximal end and a distal end, at least one of the proximal end or the distal end of the elongated spring element is fixed to the first shaft member;
   a first capture member operably engaged to an inner wall of the proximal end portion of the first shaft member, the proximal end of the elongated spring element supported by the capture member; and
   a second capture member operably engaged to the inner wall, the distal end of the elongated spring element supported by the second capture member.

2. The electrosurgical forceps according to claim 1, wherein the second shaft member is rigid along its length.

3. The electrosurgical forceps according to claim 1, wherein the first and second shaft members are configured to resist flexing during approximation of the proximal end portions thereof.

4. The electrosurgical forceps according to claim 1, wherein the elongated spring element is a cantilever spring.

* * * * *